(12) United States Patent
Jan et al.

(10) Patent No.: US 7,945,020 B2
(45) Date of Patent: May 17, 2011

(54) MEDICAL INSPECTION APPARATUS

(75) Inventors: Meei-Ling Jan, Taoyuan County (TW); Po-Hsiu Kuo, Taoyuan County (TW)

(73) Assignee: Institute of Nuclear Energy Research Atomic Energy Council, Executive Yuan, Taoyuan County (TW)

( * ) Notice: Subject to any disclaimer, the term of this patent is extended or adjusted under 35 U.S.C. 154(b) by 110 days.

(21) Appl. No.: 12/572,322

(22) Filed: Oct. 2, 2009

(65) Prior Publication Data

US 2010/0086103 A1    Apr. 8, 2010

(30) Foreign Application Priority Data

Oct. 3, 2008   (TW) ............................... 97138244 A

(51) Int. Cl.
*A61B 6/04* (2006.01)
*G01N 23/04* (2006.01)
(52) U.S. Cl. ......................................... 378/63; 378/209
(58) Field of Classification Search .................... 378/37, 378/62, 63, 209, 68; 5/601, 110, 621
See application file for complete search history.

(56) References Cited

U.S. PATENT DOCUMENTS

| | | | |
|---|---|---|---|
| 5,305,365 A | 4/1994 | Coe | |
| 5,855,554 A | 1/1999 | Schneider et al. | |
| 6,886,198 B2 * | 5/2005 | Marin et al. | ...................... 5/601 |
| 6,922,859 B2 | 8/2005 | Gagnon et al. | |
| 7,264,592 B2 | 9/2007 | Shehada | |
| 7,266,407 B2 | 9/2007 | Li et al. | |
| 7,526,066 B2 * | 4/2009 | Koshnitsky et al. | ............ 378/68 |
| 7,699,783 B2 * | 4/2010 | Hanover et al. | ............... 600/459 |

* cited by examiner

*Primary Examiner* — Irakli Kiknadze
(74) *Attorney, Agent, or Firm* — WPAT, PC; Justin King

(57) ABSTRACT

The present invention provides a medical inspection apparatus which comprises a frame, an inspection module, and a motion control unit. The frame has a couch for positioning a patient, a flexible broad bandage, an opening on the flexible broad bandage, and a chamber formed inside the frame at a position corresponding to the opening. The inspection module is disposed in the chamber and is configured with at least one detector. The motion control unit is coupled to the inspection module for actuating the inspection module to perform a vertical movement and a rotating movement and for adjusting the relative position between the at least one detector.

13 Claims, 11 Drawing Sheets

MEDICAL INSPECTION APPARATUS

FIELD OF THE INVENTION

The present invention relates to a medical apparatus, and more particularly, to a medical apparatus for executing cancer screening, diagnosis, detection, or therapy monitoring.

BACKGROUND OF THE INVENTION

According to the statistics from the Department of Health in Taiwan, breast cancer is the fourth leading cause of cancer deaths in women today and is the most common cancer among women. There are about one thousand women deceased from the disease which accounts for near 10% of all the women die from cancers. However, breast cancer in not incurable but because most breast cancers that are found only when they are causing symptoms and are more likely to have already spread beyond the breast. In contrast, breast cancers found during screening exams are more likely to be smaller and still confined to the breast. Therefore, through an early detection means that allows earlier diagnosis of breast cancer, not only the chance for diagnosing breast cancer at an early stage is improved and the treatment as well, but also the change for breast cancer recurrence can be reduced.

As we enter the twenty-first century, we are enjoying an abundant lifestyle with increasing income, but the same time that our society as well as the environment around us are changing therewith which leads to the rising in breast cancer rate and also the risk for young women to develop breast cancer is increasing. Thus, it is vital to have sophisticated imaging equipments capable of performing screening exams for early breast cancer detection, since by which not only the person die from the disease can be reduced as breast cancers found during screening exams are more likely to be smaller and still confined to the breast that are easier to be cured, but also the waste in our medical resource and exhaust in our society cost are reduced. Conventionally, there are several imaging means currently available for breast cancer assessment, such as X-ray mammography, ultrasonic mammography, magnetic resonance imaging (MRI), positron emission tomography (PET) and single photon emission computed tomography (SPECT), which are all useful tools for helping physicians with regard to breast cancer diagnosis and identification and thereby, improves the chances that breast cancer can be diagnosed at an early stage and treated successfully.

Please refer to FIG. 1, which shows a breast lesion localization device disclosed in U.S. Pat. No. 5,855,554. The aforesaid breast lesion localization device employs a chest support 11 for holding the patient in a slightly rotated prone position allowing the breast tissue 14 to hang downward and fit through an opening 13 in the supporting plate 11 of the chest support 10, while holding the other breast against the subject away from the imaging region. The breast tissue 14 is fixedly secured by a holding device 15 for enabling an interventional device 16 fitting in the holding device 15 to detect whether there is a lesion existed in the breast tissue 14.

There is another breast inspection apparatus, disclosed in U.S. Pat. No. 7,266,407, which employs a plurality of microwave-pulse sources for radiating a breast of a patient to detect whether there is a lesion existed in the breast as the patient is lying on a support while allowing the breast to be exposed to radiation of the plural microwave-pulse sources through an opening of the support. Moreover, there is another breast inspection apparatus disclosed in U.S. Pat. No. 7,264,592, which is a breast tomography scanner capable of using an ultrasonic transducer mounted on a chamber to inspect a breast a patient as the patient is lying on a support in a prone position while allowing the breast to dangle through an opening on the support and submerged in a fluid filled in the chamber of the ultrasonic transducer.

Another breast inspection device, being disclosed in U.S. Pat. No. 5,305,365, is a mammography system with a variable angle adjustable to a standing patient in forwardly leaning posture to maximize breast tissue exposure to the mammography by gravity. In addition, there is a table for positioning a patient for a medical procedure on a breast, disclosed in U.S. Pat. No. 6,922,869, which is a plate being surrounded by a solid frame that is configured with an aperture for the breast to be pendantly suspended therethrough.

SUMMARY OF THE INVENTION

The object of the present invention is to provide a medical inspection apparatus, capable of providing support to a portion of a patient's body by the use of a flexible broad bandage or several bandages while configuring an opening on the flexible band for allowing a pendulus inspected tissue, such as a breast, to pass therethrough and the same time providing a push-extrusion support on the inspected tissue for shaping, centralizing, and stabilizing the same. As the flexible broad bandage is made of a soft flexible elastic material, it can be deformed by the contact with detectors when the detectors are raised to perform a medical inspection so that the detectors are able to perform the medical inspection at a position very close to the patient's chest wall and thus its effective inspection field is enlarged comparing to those conventional support couch whose inspection are generally restricted by dead zones caused from the thickness of the couch supporting the patient.

Another object of the invention is to provide a medical inspection apparatus, configured with detectors whose position are adjustable for preparing the same to perform a medical inspection onto a part of patient's body to be inspected, in which an opening is formed on a support of the medical inspection apparatus at a position corresponding to its detectors for allowing an inspected part of a patient lying on the support to be positioned corresponding to the detector.

Furthermore, another object of the invention is to provide a medical inspection apparatus, not only capable of performing various medical inspections as its detectors are coupled to a motion control unit for enabling the same to be raised to a position that it is exposed outside an opening formed on a couch for supporting a patient's body, but also capable of alleviating the discomfort of a patient as she/her is lying on the supporting couch in a prone position since the height measured between the couch and a ground level as well as the tilting angle of the prone position are all designed to be adjustable in the medical inspection apparatus.

In an exemplary embodiment, the present invention provides a medical inspection apparatus, comprising: a frame, an inspection module, and a motion control unit. The frame with couch has a flexible broad bandage on couch opening for supporting the chest of a patient, an opening on the flexible broad bandage, and a chamber formed inside the frame at a position corresponding to the opening. The inspection module is disposed in the chamber and is configured with at least one detector. The motion control unit is coupled to the inspection module for actuating the at least one detector to perform an up-down movement, a translation movement and a rotating movement.

Preferably, the frame further comprises: a tension adjusting unit, being disposed at a position relative to the two sides of the flexible broad bandage, to be used for adjusting the tension of the flexible broad bandage, for allowing the same to providing a push-extrusion support to a tissue to be inspected while shaping, centralizing, and stabilizing the inspected tissue in a manner that an inspection area of the medical inspection apparatus with regard to the inspected tissue is enlarged.

Preferably, the motion control unit further comprises: a motion module and a rotation module, in which the motion module is coupled to the inspection module and comprised of: a shifting member, coupled to the at least one detector for actuating the same to move and thus adjusting the relative positions between the at least one detector; and a raising member, coupled to the shifting member for providing power to actuate the inspection module to raise/descend and thus adjust the attitude of the same; and the rotation module is coupled to the motion module for providing power to rotate the same.

Preferably, the at least one detector driven to move by the vertical movement is capable of being raised to a position that it is exposed outside the opening of the flexible broad bandage.

Preferably, the frame is configured with a couch of cambered surface in a manner that the flexible broad bandage of tension adjusting ability is disposed on the cambered surface of the couch while forming an opening on the couch at a position corresponding to the opening of the flexible broad bandage, so that the couch is used for supporting the whole body of the patient.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 1:
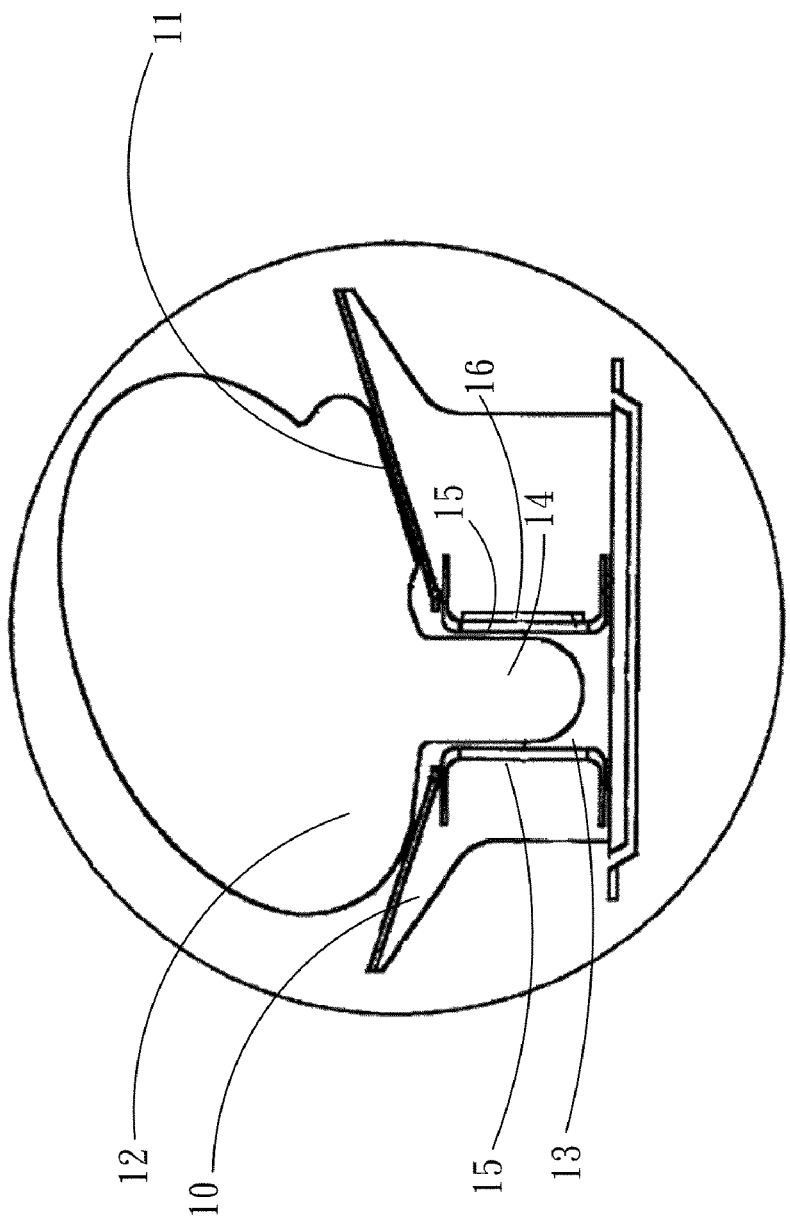
FIG. 1 shows a breast lesion localization device disclosed in U.S. Pat. No. 5,855,554.
Figure 2A:
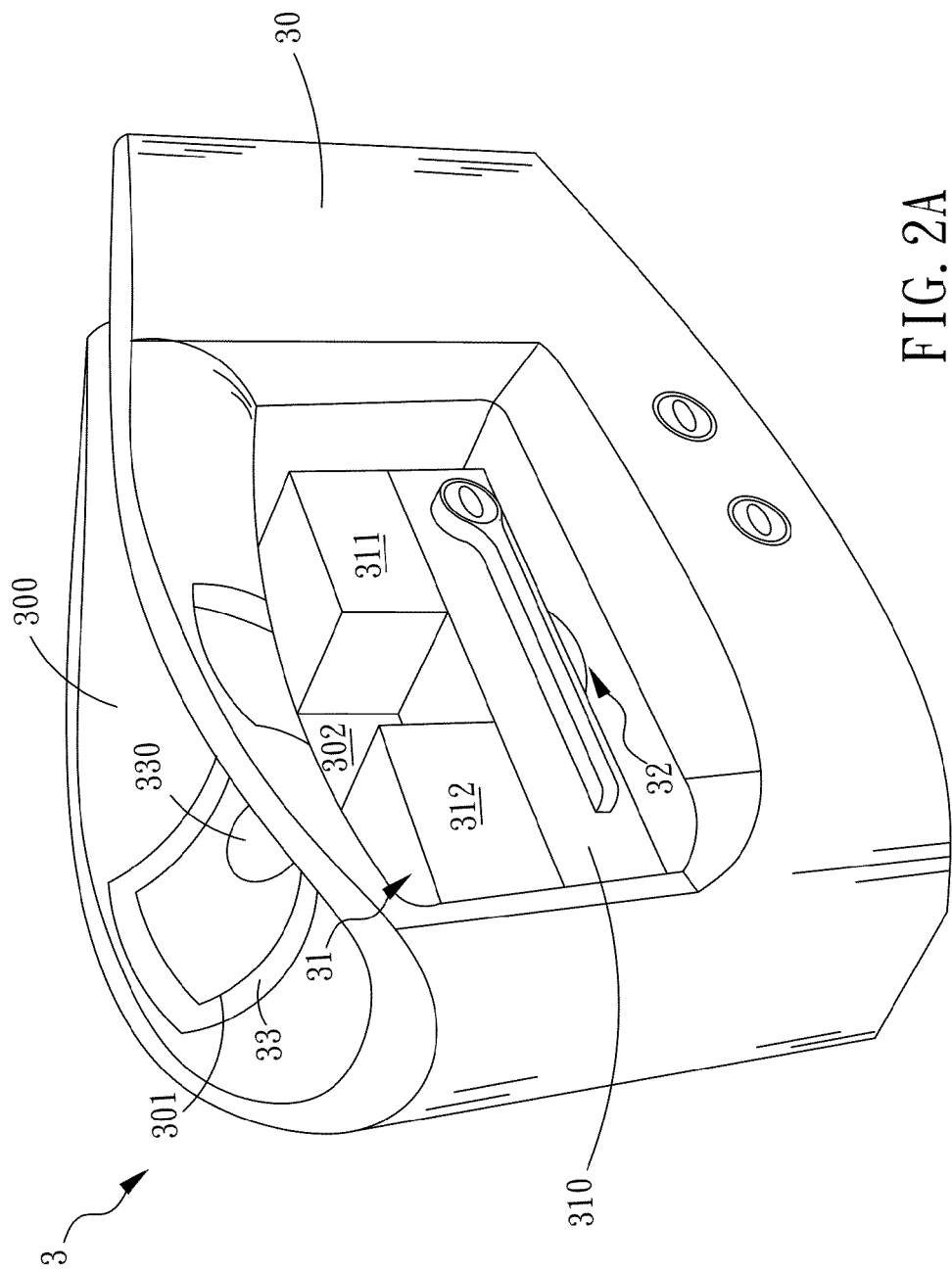
FIG. 2A is a three-dimensional view of a medical inspection apparatus according to an exemplary embodiment of the invention.
Figure 2B:
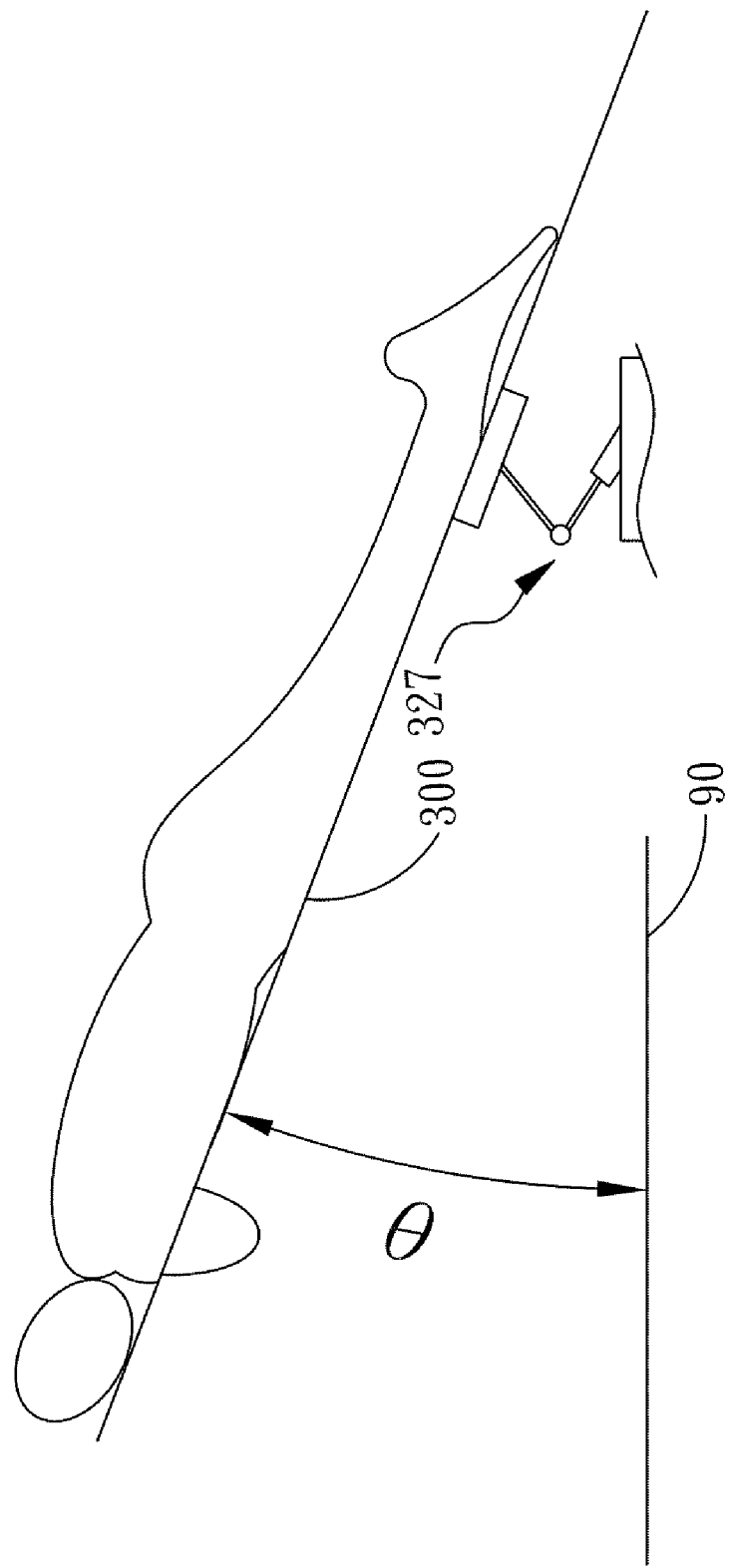
FIG. 2B shows a couch used in a medical inspection apparatus of the invention in a tilting angle.

Please refer to FIG. 2A, which is a three-dimensional view of a medical inspection apparatus according to an exemplary embodiment of the invention. In FIG. 2A, the medical inspection apparatus 3 comprises: a frame 30, an inspection module 31 and a motion control unit 32. The frame 30 has a couch located at the top thereof to be used for supporting an inspected object or a patient to lie thereon in a position such as lying on one's back, lying on one's stomach or lying on one's side. In this embodiment, the couch 300 is substantially a plate formed with a cambered surface and an opening 301, in that the opening 301 is located at a position corresponding to a chamber 302 formed inside the frame 30. As shown in FIG. 2B, the couch 300 is inclined to form a tilting angle θ included between the couch 301 and a ground level 90, by which the comfort of the patient being inspected by the medical inspection apparatus 3 can be ensured. Preferably, the tilting angle θ is adjustable in a range between 5 degrees and 15 degrees and is adjusted by the use of a tilt adjustment module 327. In this embodiment, the tilt adjustment module 327 is an assembly of linkage rods and hydraulic components, but is not limited thereby, and as it is known to those skilled in the art, it is not described further herein. it needs not necessarily have been construed to be limitative as we are advised now There is a flexible broad bandage 33 being disposed on the couch 300 at a position corresponding to the opening 301 of the couch 300. The flexible broad bandage 33 is made of flexible elastic material such as elastic fabric or elastic band, etc., that is capable of push-extrusion on a tissue to be inspected for shaping, centralizing, and stabilizing the same. The flexible broad bandage 33 needs not necessarily have been constructed to be limitative as one broad bandage. More than one bandages to form a elastic support can have the same function. The flexible broad bandage 33 is formed with an opening 330 at a position corresponding to the opening 301 of the couch 300 that it is provided for the inspected tissue to pass therethrough. In this embodiment, there can be various flexible broad bandages with openings 330 of different sizes that are provided and selected to be placed on the couch 300 according to the type and size of the tissue to be inspected. As soon as the inspected tissue is disposed to pass through the opening 330 of the flexible broad bandage 33, it is excluded by the elasticity of the flexible broad bandage 33 because of naturally gravity and thus the tissue is shaped, centralized, and stabilized for preparing the same for inspection. On the other hand, since the flexible broad bandage is made of a flexible elastic material, it can be deformed by the contact with detectors when the detectors are raised to perform a medical inspection so that the detectors are able to perform the medical inspection at a position very close to the patient's chest wall thus its effective inspection field is enlarged comparing to those conventional support couch whose inspection are generally restricted by dead zones caused from the thickness of the couch supporting the patient. and thus its effective inspection field is enlarged comparing to those conventional support couch whose inspection are generally restricted by dead zones caused from the thickness of the couch supporting the patient. Therefore, by the use of the flexible broad bandage 33, the conventional dead zone problem caused by rigid supporting plate is eliminated so that the inspection field as well as its accuracy can be improved. The inspection module 31, being received inside the chamber 302, is comprised of: a platform 310 and a pair of detectors 311, 312, in which the pair of detectors 311, 312 is mounted on the platform 310. In this embodiment, the detectors 311, 312 are paired for enabling the two to detect a gamma photon pair emitted from a positron source. However, it is not limited thereby. For instance, it can be used for detecting a gamma ray emitted from a single-photon source inside a tissue to be inspected, or for detecting an X-ray penetrating a tissue to be inspected, or for detecting one particle selected from the group consisting of: an infrared photon emitted from a tissue to be inspected, and an infrared photon penetrating a tissue to be inspected. It is noted that when the radiation source of the medical inspection apparatus is an X-ray source or a single-photon source, only one detector will be sufficient for the detection. Please refer to FIG. 3, which is a schematic diagram showing the connection between a motion control unit and an inspection module in a medical inspection apparatus of the invention. The motion control unit 32 is coupled to the inspection module 31 for actuating the inspection module 31 to perform a vertical movement, a translation movement as well as adjusting the positions of the pair of detectors 311, 312. The motion control unit 32 includes a motion module 320 and a rotating module 321. The motion module 320 is mounted on the platform 310 and is comprised of a shifting member 322 and a raising member 323, in which the shifting member 322 is coupled to the pair of the detectors 311, 312 for actuating the same to move and thus adjusting the relative positions between the two detectors 311, 312.

Figure 3:
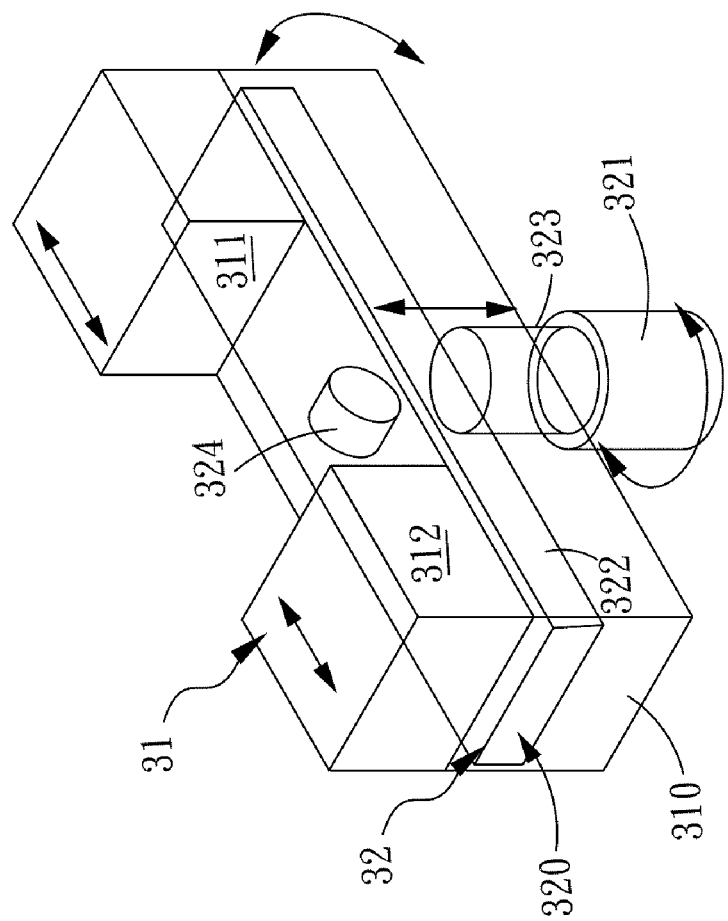
FIG. 3 is a schematic diagram showing the connection between a motion control unit and an inspection module in a medical inspection apparatus of the invention.
Figure 4:
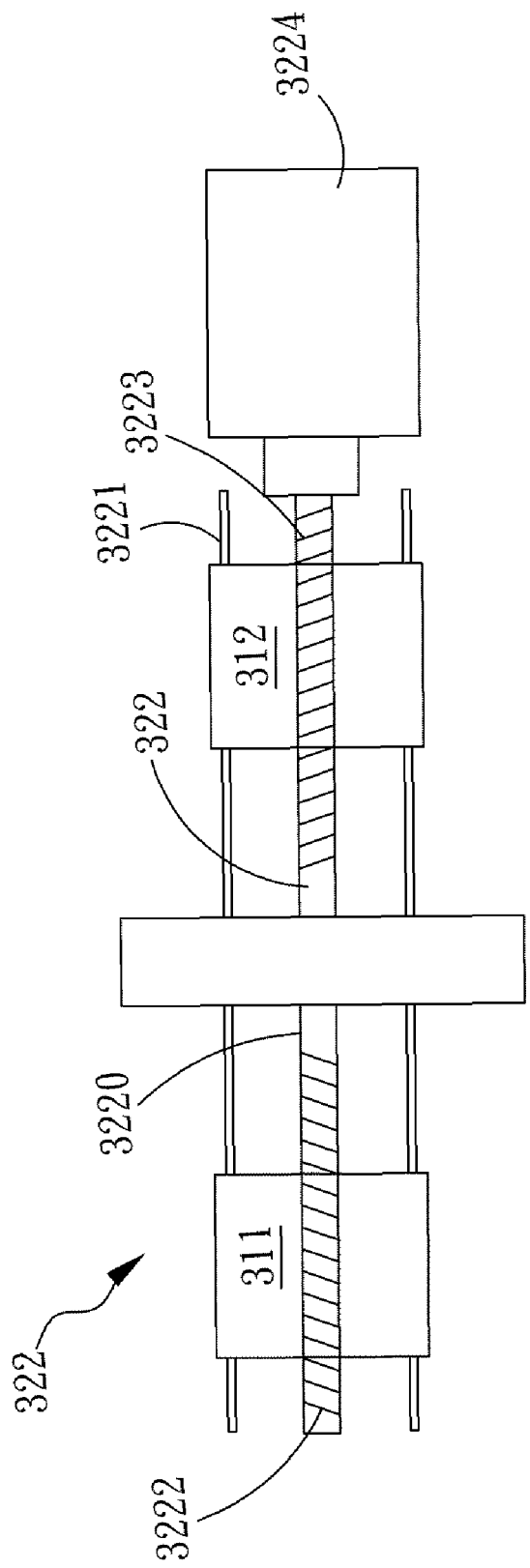
FIG. 4 is a schematic diagram showing a shifting member of the invention.
Figure 5:
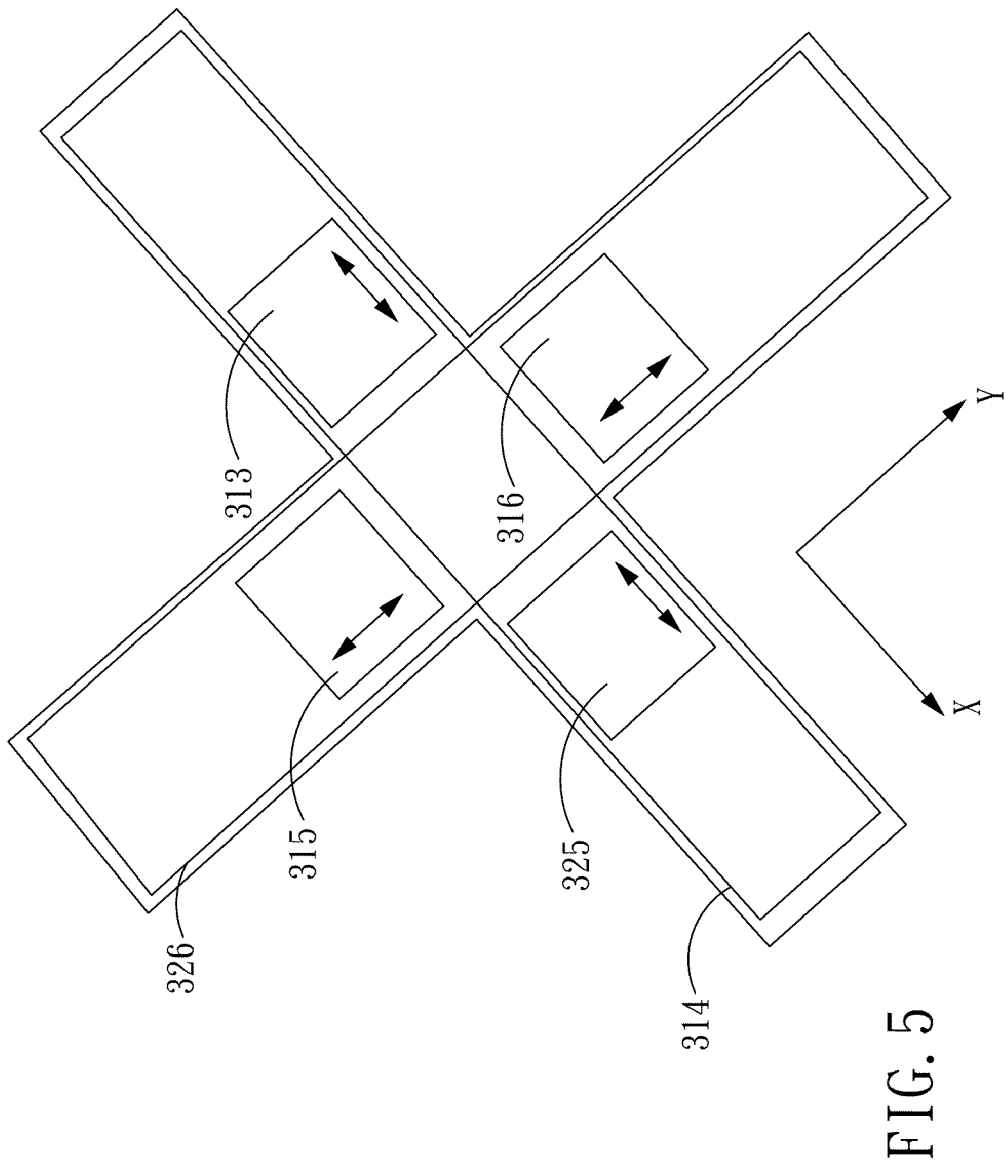
FIG. 5 is a schematic diagram showing how the detectors are arranged in the medical inspection apparatus according to an exemplary embodiment of the invention.

Please refer to FIG. 4, which is a schematic diagram showing a shifting member of the invention. For enabling the two detectors 311, 312 to move in relative to each other, the two detectors 311, 312 are respectively connected to different portions of a screw rod 3220 of opposite screws and a leading bar 3221. It is noted that the screw 3222 of the portion of the screw rod 3220 connected to the detector 311 is rotating opposite to the screw 3223 of another portion the screw rod 3220 connected to the detector 312 so that when the screw rod 3220 is driven to rotate by a driving device 3224, the two detectors 311, 312 will be driven to move in directions opposite to each other. However, it is known to those skilled in the art that despite of the aforesaid mechanism, there are other mechanisms capable of moving the two detectors in opposite directions, e.g. by connecting the two detectors respectively to two different linear guide rails, the motions of the two detectors can be controlled simply by sending a signal to the two liner guide rails. Although there is a pair of detectors 311, 312 being arranged in the medical inspection apparatus of the embodiment of FIG. 3, there can be more or less detectors being configured in the medical inspection apparatus and thus is not limited by the two shown in the embodiment of FIG. 3. Please refer to FIG. 5, which is a schematic diagram showing how the detectors are arranged in the medical inspection apparatus according to an exemplary embodiment of the invention. In FIG. 5, there are four detectors 313~316 in this embodiment, in which the detectors 313, 314 are arranged on the shifting member 325 while another two detectors 315, 316 are arranged on another shifting member 326. The shifting member 315 is used for controlling the two detector 313, 314 to move relatively in an X-axis direction, as indicated in the XY-axes Cartesian coordinate system shown in FIG. 5, i.e. by the linear translation motion caused by the shifting member 315, the two detectors 313, 314 can be driven to move close to or away from each other. Similarly, the shifting member 326 is used for controlling the two detectors 315, 316 to move relatively in a Y-axis direction. The aforesaid moving principle can also being applied to the medical inspection apparatus with three detectors, that the relative positions of the three detectors are controlled by the shifting members for enabling they to move close to or away from each other.

In the embodiment shown in FIG. 3, the raising member 323 is coupled to the inspection module 31 for providing power to actuate the inspection module 31 to raise/descend and thus adjust the attitude of the same. There can be various types of mechanisms suitable for the raising member 323, such as the hydraulic mechanism or a raising mechanism utilizing screw rods, that they all are known techniques for those skilled in the art and thus are not described further herein. The rotating module 321 is coupled to the motion module 320 for providing power to rotate the same. In this embodiment, the rotating module 321, which can be a servo motor or a step motor, is used as a power source for enabling the inspection module 31 to rotate about a Z-axis, as indicated in the Cartesian coordinate system shown in FIG. 3. Moreover, the motion control unit is further configured with a tilt adjustment module 324, which is used for adjusting a tilting angle of the inspection module 31. Generally, the tilt adjustment module 324 can be a servo motor or a step motor that is used for driving the inspection module 31 to rotate about an X-axis, as indicated in the Cartesian coordinate system shown in FIG. 3.

Figure 6:
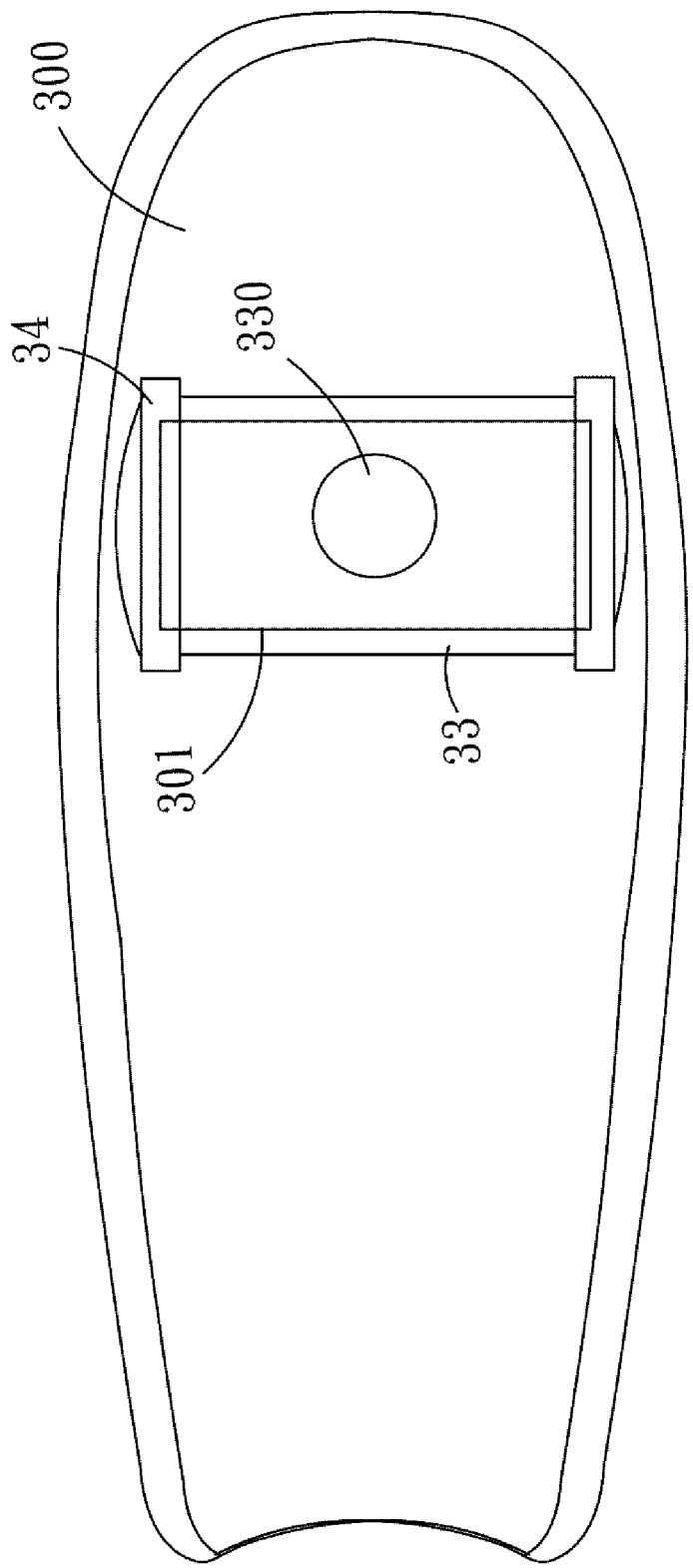
FIG. 6 is a top view of a medical inspection apparatus of the invention.

Please refer to FIG. 6, which is a top view of a medical inspection apparatus of the invention. In FIG. 6, in addition to the flexible broad bandage 33 fitted around the opening 301, there is a tension adjusting unit 34 being disposed at a position relative to the two sides of the flexible broad bandage 33 to be used for adjusting the tension of the flexible broad bandage 33. The tension adjustment unit 34 is used for adapting the flexible broad bandage 33 for patients of different weights in a manner that the flexible broad bandage 33 can be prevented from being deformed severely or even damaged by those heavy patients. For instance, when the flexible broad bandage 33 is severely deformed, not only the inspected tissue dangling through the opening 301 is dropped and thus might not be positioned correctly for the inspection, but also such deformation might cause discomfort to the patient. Therefore, it is preferred to have the tension adjustment unit 34 for adapting the tension of the flexible broad bandage 33 for patients of different weights, by that the weight the patient relating to the portion that is in contact with the flexible broad bandage 33 can be support properly.

Figure 7:
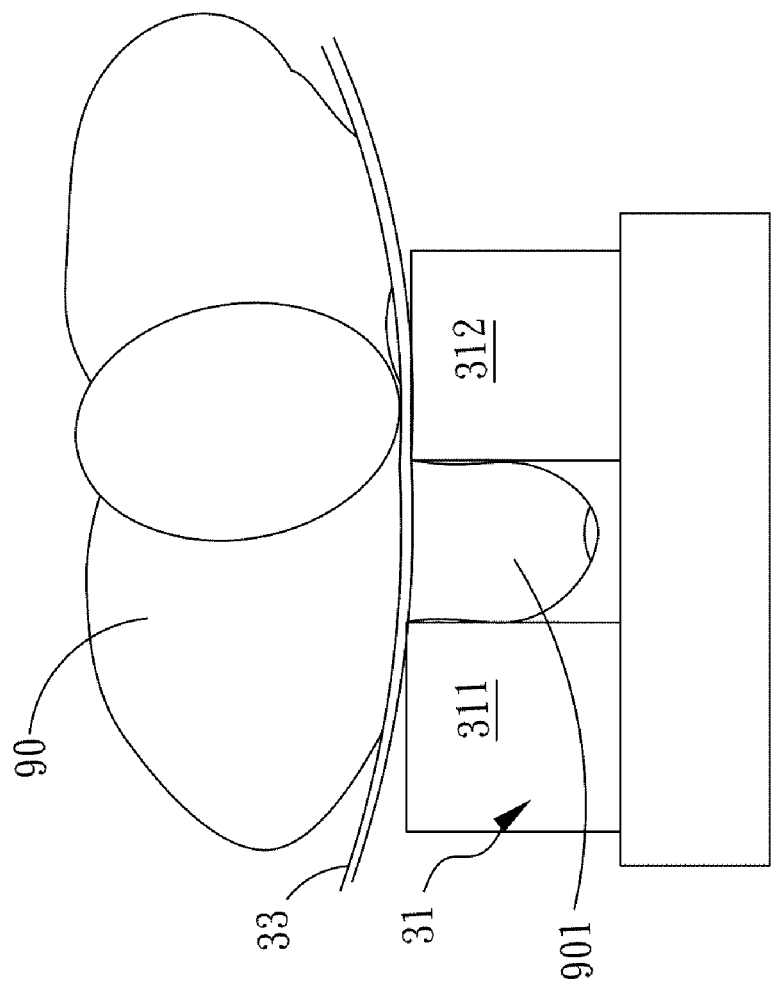
FIG. 7 is a schematic diagram showing how the medical inspection apparatus can be used according to an embodiment of the invention.
Figure 8:
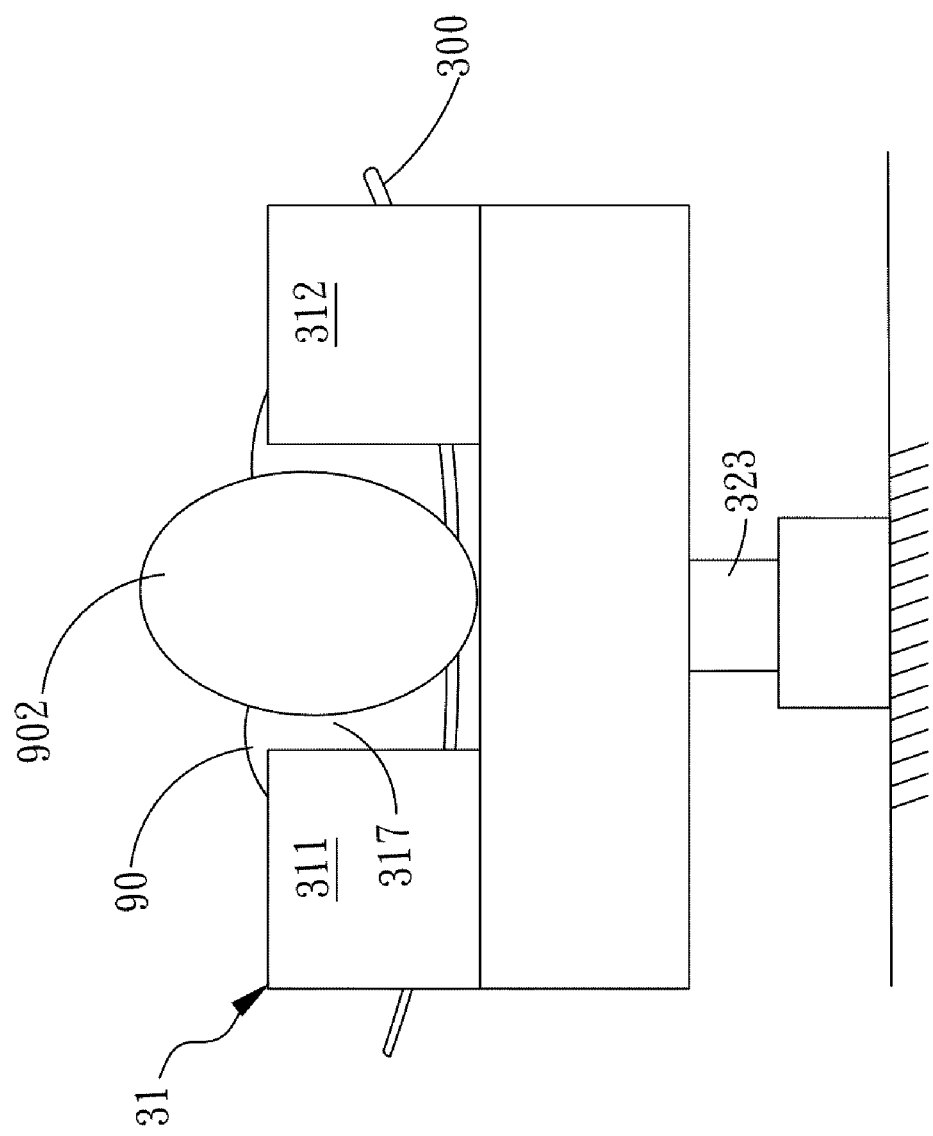
FIG. 8 is a schematic diagram showing the medical inspection apparatus is used for inspecting a patient lying on one's back according to another embodiment of the invention.
Figure 9:
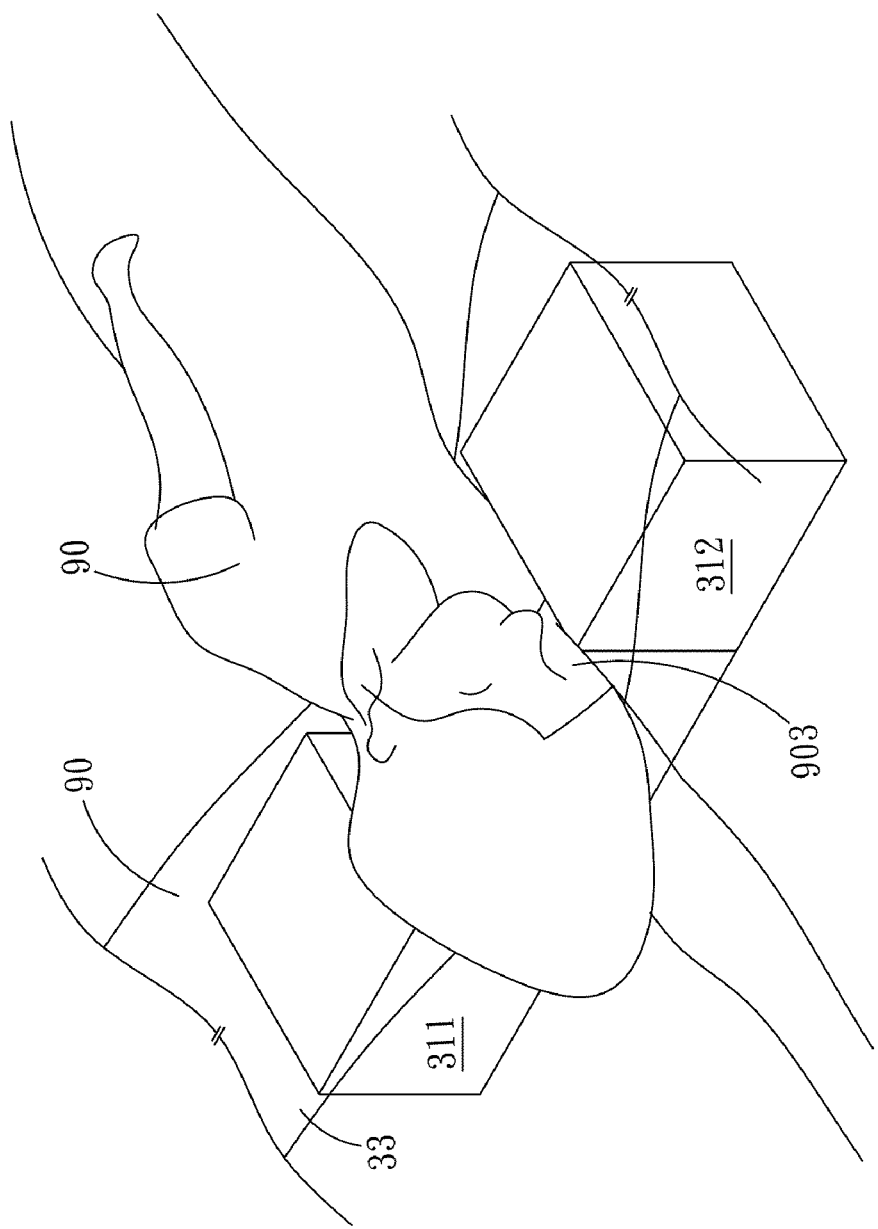
FIG. 9 is a schematic diagram showing how the medical inspection apparatus is used for inspecting a patient lying on one's side according to further another embodiment of the invention.
Figure 10:
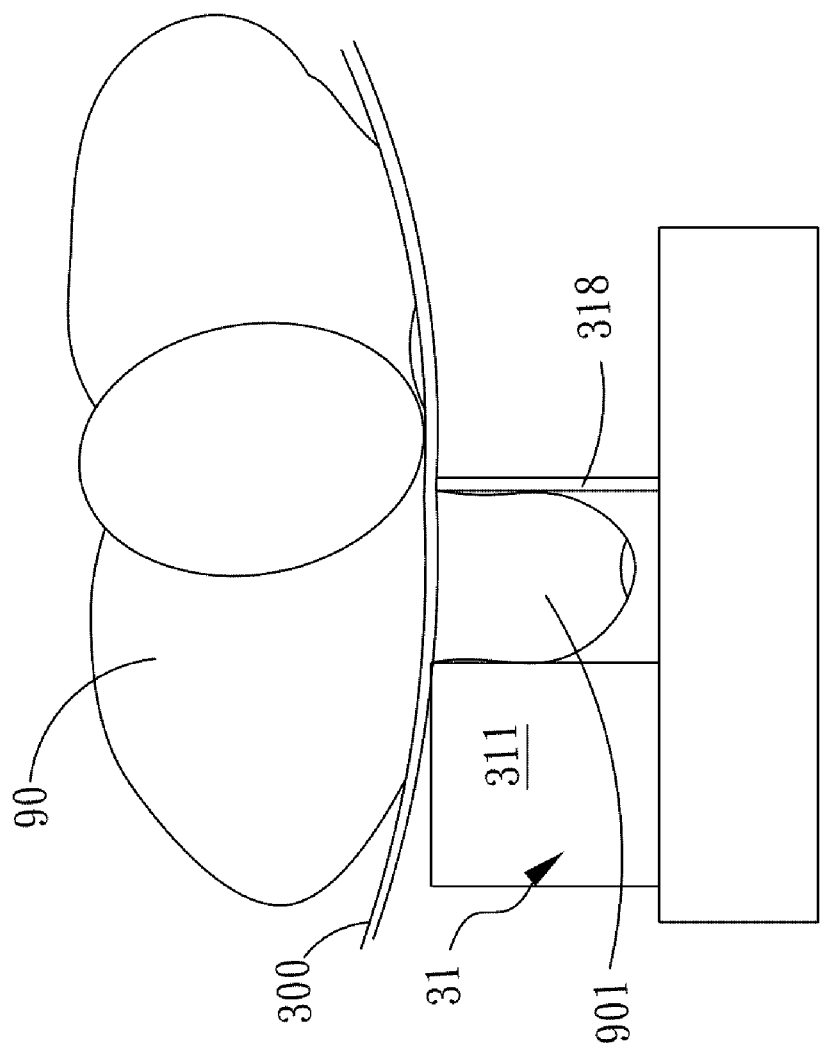
FIG. 10 is a schematic diagram showing the condition when there is only one detector being used in the medical inspection apparatus according to yet another embodiment of the invention.

Please refer to FIG. 7, which is a schematic diagram showing how the medical inspection apparatus can be used according to an embodiment of the invention. In this embodiment, the detectors 311, 312 are scintillating crystal detectors, which are used for detecting the gamma pairs generated from the annihilation between positrons and electrons. In a breast inspection, the patient 90 injected with a radioisotope labeled medicine is directed to lie on couch 300 in a prone position for pressing his/her chest on the flexible broad bandage 33 while enabling the breast 901 to be inspected to hang downward and fit through the opening and thus to dangle at a position between the two detectors 311, 312. Thereafter, by the use of the shifting member, the positions of the two detectors 311, 312 are adjusted for enabling the two to move near the inspected breast 901 so that they can detect the gamma photon pairs emitted from positron radiosource inside the inspected breast 901. Please refer to FIG. 8, which is a schematic diagram showing how the medical inspection apparatus can be used according to another embodiment of the invention. Despite of the breast, it is noted that the medical inspection apparatus of the invention can be used for inspection other body parts. As shown in FIG. 8, after removing the flexible broad bandage 33, the inspection module 31 can be raised by the raising member 323 to a position that it is exposed outside the opening of the couch 300 while forming a space 317 between the two detectors 311, 312. The space 317 is suitable for accommodating the body part that is to be inspected, such as armpit, head, hand, leg or waist, while the patient is directed to lie on one's back or on one's side, as those shown in FIG. 8 and FIG. 9. FIG. 8 shows the medical inspection apparatus is used for inspection the head of a patient as he/she is directed to lie on one's back. FIG. 9 shows the medical inspection apparatus is used for inspection the armpit of a patient as he/she is directed to lie on one's side. Please refer to FIG. 10, which is a schematic diagram showing the condition when there is only one detector being used in the medical inspection apparatus according to yet another embodiment of the invention. From the previous description, it is noted that when the radiation source of the medical inspection apparatus is an X-ray source or a single-photon source, only one detector 311 will be sufficient for the detection. However, for stabilizing and compressing the inspected tissue, a fixing plate 318 can be arranged at a position corresponding to the single detector 311.

To sum up, the present invention provides a medical inspection apparatus, configured with a detector whose position is adjustable for preparing the same to perform a medical inspection onto a tissue to be inspected, in which an opening is formed on a support of the medical inspection apparatus at a position corresponding to its detector for allowing an inspected tissue of a patient lying on the support to be positioned corresponding to the detector.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. A medical inspection apparatus, comprising:
   a frame, further comprising:
      at least one flexible broad bandage with tension adjusting ability;
      a chamber, formed inside the frame; and
      an opening, formed on the flexible broad bandage at a position corresponding to the chamber;
   an inspection module, disposed in the chamber and being configured with at least one detector; and
   a motion control unit, coupled to the inspection module for actuating the inspection module to perform a vertical movement, a translation movement as well as adjusting the position of the at least one detector.

2. The medical inspection apparatus of claim 1, further comprising:
   a tension adjusting unit, being disposed at a position relative to the two sides of the flexible broad bandage to be used for adjusting the tension of the flexible broad bandage.

3. The medical inspection apparatus of claim 1, wherein the at least one detector is configured for detecting gamma photon pairs emitted from positron tracer inside a tissue to be inspected in a respective manner.

4. The medical inspection apparatus of claim 1, wherein the at least one detector is configured for detecting an X-ray penetrating a tissue to be inspected.

5. The medical inspection apparatus of claim 1, wherein the at least one detector is configured for detecting gamma rays emitted from single-photon radiosource inside a tissue to be inspected.

6. The medical inspection apparatus of claim 1, wherein the at least one detector is configured for detecting one particle selected from the group consisting of: an infrared photon emitted from a tissue to be inspected, and infrared photons penetrating a tissue to be inspected.

7. The medical inspection apparatus of claim 1, wherein the motion control unit further comprises:
   a motion module, coupled to the inspection module and being comprised of:
      a shifting member, coupled to the at least one detector for actuating the same to move and thus adjusting the relative positions between the at least one detector; and
      a raising member, coupled to the inspection module for providing power to actuate the inspection module to raise/descend and thus adjust the attitude of the same;
   a rotating module, coupled to the motion module for providing power to rotate the same.

8. The medical inspection apparatus of claim 7, wherein the motion control unit further comprises:
   a tilt adjustment module, for adjusting a tilting angle of the inspection module.

9. The medical inspection apparatus of claim 1, wherein the at least one detector, being driven to move by the vertical movement, is capable of being raised to a position that it is exposed outside the opening of the flexible broad bandage.

10. The medical inspection apparatus of claim 1, wherein the frame further comprises:
    a couch, having an opening formed at a position corresponding to the opening of the flexible broad bandage.

11. The medical inspection apparatus of claim 10, wherein the couch of formed with a cambered surface.

12. The medical inspection apparatus of claim 10, wherein the couch is inclined by a tilting angle.

13. The medical inspection apparatus of claim 12, wherein the tilting angle is adjustable in a range between 5 degrees and 15 degrees.

* * * * *